United States Patent [19]
Exline et al.

[11] Patent Number: 5,925,013
[45] Date of Patent: Jul. 20, 1999

[54] IRRIGATION AND EVACUATION CANNULA

[76] Inventors: Donald D. Exline, 1101 E. Alan, Carrollton, Tex. 75006; William A. Pierce, 6156 Richmond Ave., Dallas, Tex. 75214

[21] Appl. No.: 08/824,849

[22] Filed: Mar. 26, 1997

[51] Int. Cl.$^6$ .................................................. A61M 1/00
[52] U.S. Cl. ................... 604/32; 604/35; 604/249
[58] Field of Search ..................... 604/30, 31, 32, 604/33, 35, 36, 118, 119, 246, 248, 249; 137/889, 892, 893

[56] References Cited

U.S. PATENT DOCUMENTS

| | | | |
|---|---|---|---|
| 2,964,056 | 12/1960 | Speer | 137/589 |
| 3,157,201 | 11/1964 | Littmann | 137/625.47 |
| 4,668,215 | 5/1987 | Allgood | 604/30 |
| 4,696,305 | 9/1987 | von Berg | 128/673 |
| 4,776,840 | 10/1988 | Freitas et al. | 604/33 |
| 4,904,245 | 2/1990 | Chen et al. | 604/248 |
| 4,967,797 | 11/1990 | Manska | 137/625.47 |
| 5,135,026 | 8/1992 | Manska | 137/555 |
| 5,312,373 | 5/1994 | Freitas | 604/249 |

*Primary Examiner*—Wynn Wood Coggins
*Assistant Examiner*—Deborah Blyveis

[57] ABSTRACT

A cannula comprises a housing secured to a generally tubular sleeve member. The housing is provided with irrigation and evacuation fluid ports for connection to irrigation and evacuation conduits. An instrument port is formed in the housing and aligned with the sleeve member, wherein a surgical instrument can be inserted through the instrument port, housing, and sleeve member and into the bodily cavity. The instrument port includes seal members to seal against fluid leakage from the cannula with or without a surgical instrument passing through the housing and sleeve member. A valve member is rotatably carried by the housing to selectively obstruct one or more of the irrigation and evacuation ports. The valve is arranged such that the surgical instrument may remain in the housing and sleeve member during manipulation of the valve.

18 Claims, 2 Drawing Sheets

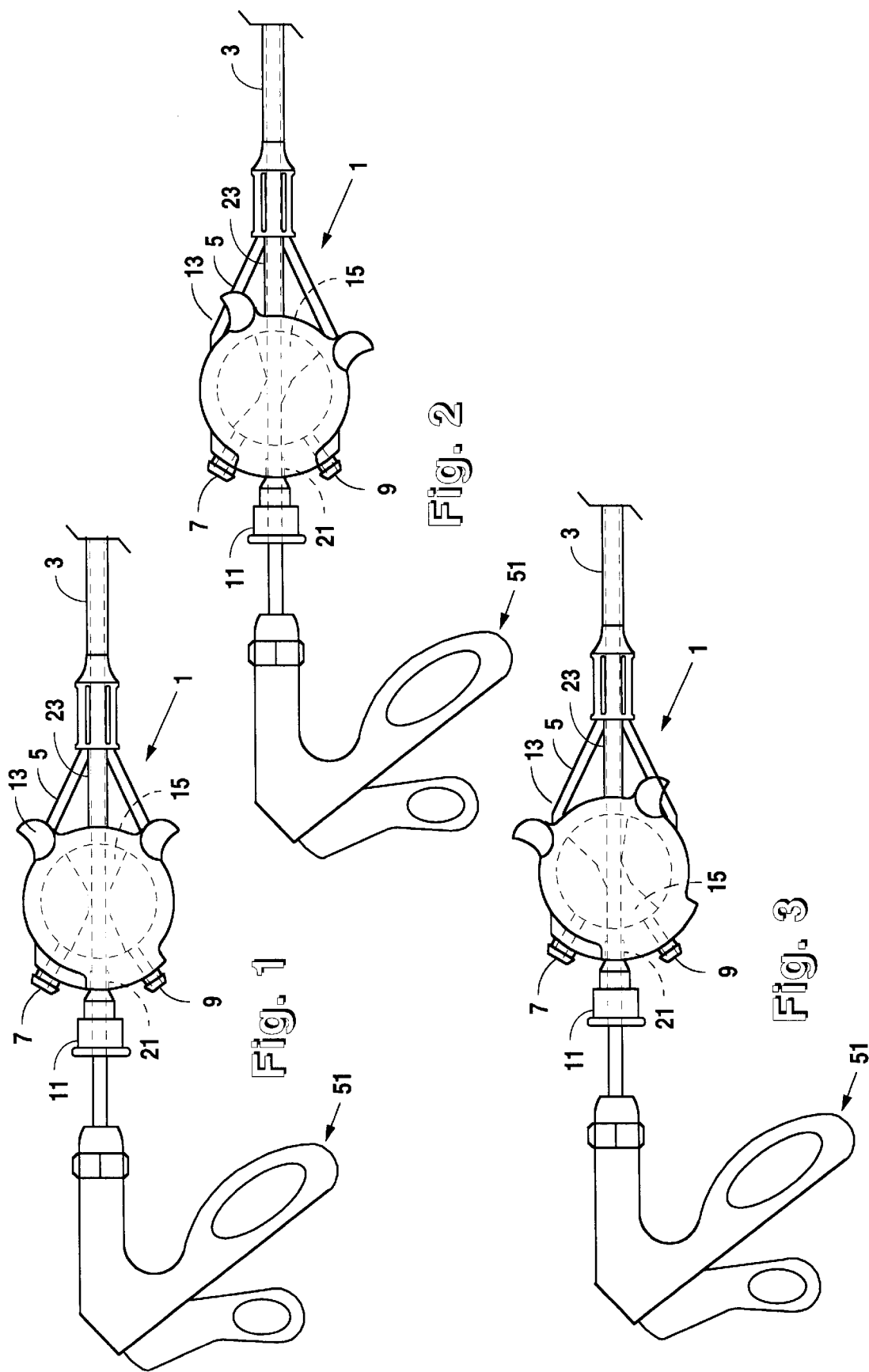

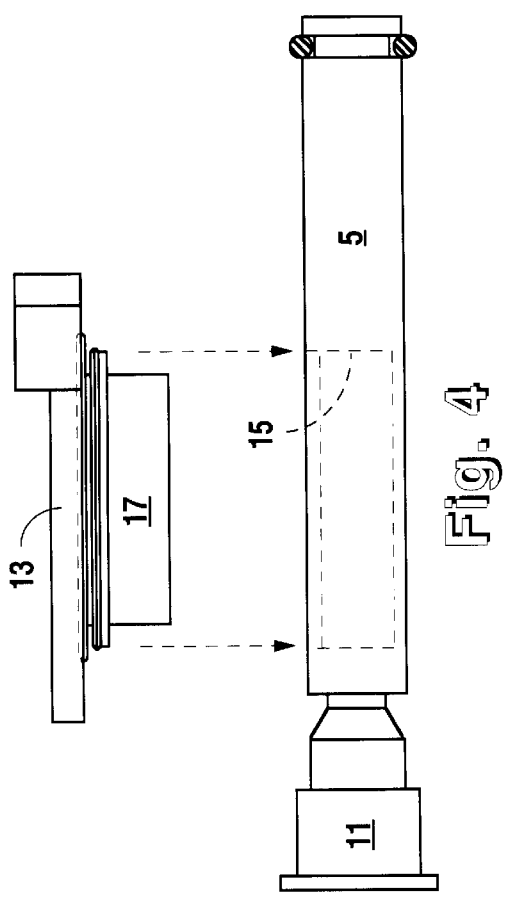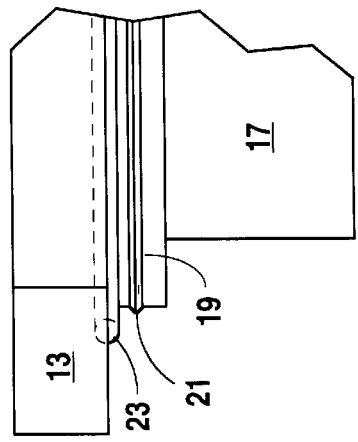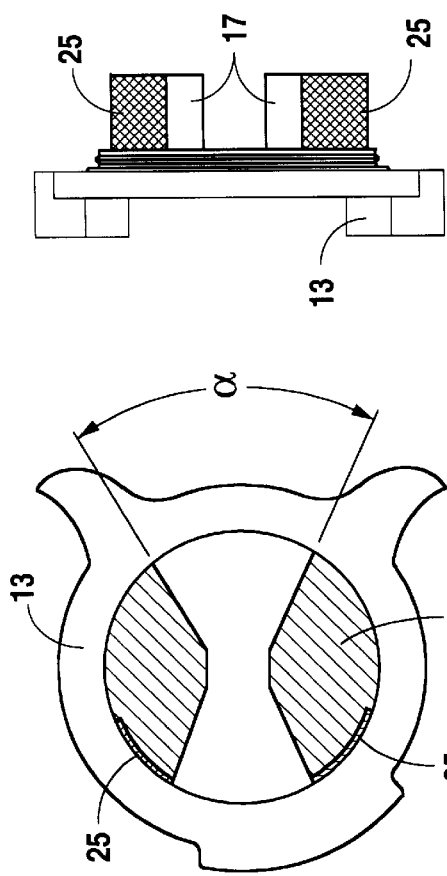

IRRIGATION AND EVACUATION CANNULA

BACKGROUND OF THE INVENTION

1. Field of the Invention

The present invention relates generally to surgical instruments. More particularly, the present invention relates to cannulae and sleeves used to irrigate and evacuate body cavities during endoscopic or minimally invasive surgery.

2. Background Information

Endoscopic surgical procedures (sometimes referred to as "laparoscopy") are becoming increasingly accepted in the medical community for many surgical procedures. In endoscopic surgery, a small incision typically is made in the abdominal wall through which a fiber-optic viewing device ("endoscope")is inserted into the abdominal or other body cavity. Other small incisions are made through which surgical instruments are passed to dissect tissue and perform other operations. Frequently, the body cavity is insufflated with an inert gas, such as $CO_2$, which provides space in which to manipulate surgical instruments and to view the area in which surgical operations are to take place. Endoscopic procedures are preferable to many conventional surgical techniques because they are less invasive and therefore permit patients to recover more quickly and reduce the rate of infection.

Because the endoscopic surgical site is enclosed within the body cavity, irrigation and evacuation of the site is rendered somewhat more difficult in endoscopic procedures than in open or conventional techniques. In both open and endoscopic surgical procedures, suction and irrigation tubes are placed in the surgical site, one to evacuate fluids and one to irrigate with fluid. Provision of two separate tubes for irrigation and evacuation is cumbersome. Commonly owned U. S. Pat. No. 4,668,215, May 26, 1987 to Allgood, discloses a valving arrangement whereby irrigation and evacuation can be accomplished with a single line or tube passed through an endoscopic cannula or sleeve. Similarly, commonly owned U.S. Pat. No. 4,776,840, Oct. 11, 1988 to Freitas et al. discloses a device for simultaneously providing irrigation and evacuation that is adapted for single-handed use. Nevertheless, a tube passes from the device, through a cannula or sleeve, and into the surgical site.

Irrigation and evacuation tubes have been combined into endoscopic cannulae or sleeves to combine previously separate apparatus into one. This cannula is passed through an incision and provides a tube through which suction may be applied to evacuate blood and other fluids from the surgical site and through which fluid may be provided to irrigate the surgical site.

To permit the surgical instrument to pass unobstructed through the irrigation and evacuation cannula or sleeve, complex valving arrangements are required to permit connection of evacuation and irrigation apparatus with the cannula. These arrangements commonly take the form of trumpet valves, which are arranged at generally right angles to the lumen or passage extending through the cannula or sleeve. Thus, during irrigation and evacuation, fluids and bits of tissue travel through a convoluted path between the irrigation and evacuation conduits, the valves, the cannula passage, and into and out of the body cavity. Examples of such prior-art cannula can be found in commonly assigned U.S. Pat. No. 5,312,373, May 17, 1994 to Freitas, and in U.S. Pat. No. 4,696,305 to Von Berg. Such prior-art cannulae are difficult to clean and sterilize, and thus to reuse. Additionally, the convoluted fluid path has generally poor fluid dynamics and makes the apparatus prone to clogging.

A need exists, therefore, for surgical irrigation and evacuation cannulae having improved valving arrangements that permit fluid to flow through the cannula in a more linear fashion and that are thus more easily cleaned and sterilized and less prone to clogging.

SUMMARY OF THE INVENTION

It is a general object of the present invention to provide an improved irrigation and evacuation cannula or sleeve for use in irrigating and evacuating a body cavity during surgery. This and other objects of the present invention are achieved by providing a cannula comprising a housing secured to a generally tubular sleeve member. The housing is provided with irrigation and evacuation fluid ports for connection to irrigation and evacuation conduits. An instrument port is formed in the housing and aligned with the sleeve member, wherein a surgical instrument can be inserted through the instrument port, housing, and sleeve member and into the body cavity. The instrument port includes seal members to seal against fluid leakage from the cannula with or without a surgical instrument passing through the housing and sleeve member. A valve member is rotatably carried by the housing to selectively obstruct one or more of the irrigation and evacuation ports. The valve is arranged such that the surgical instrument may remain in the housing and sleeve member during manipulation of the valve.

According to the preferred embodiment of the present invention, a generally circular recess is provided in the housing to receive the valve member. The irrigation, evacuation, and instrument ports are arranged about the circumference of the circular recess. The valve member and recess cooperate to define a venturi-shaped chamber within the housing.

According to the preferred embodiment of the present invention, the instrument port includes both a lip seal and an outer-diameter seal.

According to the preferred embodiment of the present invention, the valve member is selectively removable from the housing.

According to the preferred embodiment of the present invention, a fluid path extends from the instrument port, through the housing and venturi-shaped chamber and the tubular sleeve member and is generally straight to provide improved fluid flow dynamics.

According to the preferred embodiment of the present invention, a pair of seal members is disposed between the valve member and housing to seal the first and second fluid ports against fluid leakage.

According to the preferred embodiment of the present invention, a switch member may be carried by the housing to cooperate with the valve member to selectively actuate a device external to the cannula, such as an irrigation or evacuation pump, responsive to movement of the valve member.

DESCRIPTION OF THE DRAWINGS

FIGS. 1–3 are partial elevation views, partially in section, of the irrigation and evacuation cannula according to the present invention.

FIG. 4 is an exploded, side elevation view of the housing portion of the irrigation and evacuation cannula of FIGS. 1–3.

FIG. 5 is an enlarged, partial elevation view of a portion of the valve member illustrated in FIG. 4.

FIG. 6 is a plan view of the valve member illustrated in FIGS. 1–5.

FIG. 7 is a side elevation view of the valve member of FIG. 6.

FIG. 8 is a partial elevation view of a portion of the housing of the irrigation and evacuation cannula according to the preferred embodiment of the present invention.

FIG. 9 is a front view of the irrigation and evacuation cannula according to the preferred embodiment of the present invention.

DESCRIPTION OF THE PREFERRED EMBODIMENT

Referring now to the figures, FIGS. 1–3 are partial elevation views, partially in section, of the irrigation and evacuation cannula 1 according to the present invention. Irrigation and evacuation cannula 1 comprises a generally tubular sleeve member 3 having a passageway or lumen extending therethrough. Sleeve member 3 is the portion of cannula 1 that is inserted through an incision in a body wall to irrigate and evacuate a surgical site during endoscopic surgery.

Sleeve member 3 is coupled to a housing 5 by threads, and an o-ring (See FIG. 4) is provided to seal the joint against fluid loss. Housing 5 is provided with first and second or irrigation and evacuation ports 7, 9 which are arranged generally opposite sleeve member 3 and are angularly displaced less than 90° from the longitudinal axis of cannula 1. Irrigation and evacuation ports 7, 9 are adapted for connection to the conduits of fluid supply (irrigation) and vacuum or suction (evacuation) apparatus (not shown). An instrument port 11 is provided in housing 5 opposite from and aligned with sleeve 3. Instrument port 11 is provided with a conventional internal lip seal 65 and outer-diameter 70 seal, which cooperate to seal against fluid loss through port 11 whether a surgical instrument is present or not (see FIG. 9). Thus, an endoscopic surgical instrument 51 can be inserted through instrument port 11, housing 5, sleeve member 3, and into the body cavity without loss of insufflation gas through cannula 1.

A valve member 13 is received for rotation in a circular recess 15 formed in housing 5 (circular recess 15 is depicted in phantom in FIGS. 1–3). Valve member 13 is formed to cooperate with circular recess 15 in housing 5 to define a venturi-shaped chamber that is narrower or more restricted in its central portion than at its periphery. Valve member 13 selectively obstructs irrigation and evacuation ports 7, 9 which are in fluid communication with circular recess 15 and sleeve member 3.

The venturi-shaped chamber defined by valve member 13 and recess 15 permits selective obstruction of either or both of irrigation and evacuation ports 7, 9 while surgical instrument 51 extends through housing 5 and sleeve member 3, even during manipulation of valve 13.

FIGS. 1–3 illustrate irrigation and evacuation cannula 1 in three configurations, in each of which a endoscopic surgical instrument 51 extends through instrument port 11, housing 5, and sleeve member 3. In FIG. 1, both irrigation and evacuation ports 7, 9 are obstructed and closed by portions of valve member 13 and are sealed against fluid loss (the seals are described in greater detail with reference to FIG. 6). In each configuration, the seals 65, 70 of instrument port 11 prevent fluid loss around instrument 51.

FIG. 2 illustrates irrigation and evacuation cannula 1 in an irrigation mode in which irrigation port 7 is open, while evacuation port 9 is obstructed by valve member 13. In this configuration, irrigation fluid is introduced from an irrigation conduit (not shown) through irrigation port 7, housing 5, sleeve member 3, and into the body cavity.

FIG. 3 depicts irrigation and evacuation cannula 1 in an evacuation configuration in which evacuation port 9 is open and irrigation port 7 is obstructed by valve member 13. In this configuration, vacuum or suction is applied from an evacuation conduit (not shown) through evacuation port 9, housing 5, sleeve member 3, and into the body cavity.

Each of the configurations of FIGS. 1–3 is accomplished by rotating valve member 13 relative to housing 5. Because of the configuration of housing 5 and valve member 13, this rotation can occur without regard to the presence or absence of surgical instrument 51 in cannula 1. Because ports 7, 9 are angularly displaced from the longitudinal axis of cannula 1, and due to the venturi-shaped chamber defined by valve 13 and housing 5, the flow path that fluid must follow is generally straight and avoids right-angle turns, thereby promoting more efficient fluid flow and providing fewer places for debris to be caught.

FIGS. 4 and 5 are enlarged elevation views depicting the cooperation between valve member 13 and circular recess 15 in housing 5. As shown, valve member 13 includes a projection having a pair of portions 17 that together are generally circular in cross-section. Preferably, the two portions 17 of projection cooperate to define a circle about 450 mm in diameter. Thus, valve member 13 is assembled into and rotatable within circular recess 15 of housing 5. Venturi-shaped chamber is defined between portions 17 when enclosed within circular recess 15 of housing 5.

As illustrated in FIG. 5, a circular shoulder 19, which includes an annular radial projection 21, is provided on valve member 13. Shoulder 19 and radial projection 21 cooperate with corresponding recesses formed in circular recess 15 of housing 5 to provide a "snap-together" assembly that is easily assembled and disassembled. An O-ring 23 is provided in valve member 13 to seal the joint between valve member 13 and circular recess 15 against fluid loss.

FIGS. 6 and 7 are plan and elevation views of valve member 13 according to the present invention. Each projection 17 is tapered to provide an included angle of about 60° at the inlet and outlet of the venturi-shaped chamber. As shown in FIG. 6, a pair of seal members 25 is formed on the periphery of portions 17. Seal members 25 preferably are formed of Santoprene™, a polypropylene elastomer sold by Advanced Elastomer Systems of Akron, Ohio, which is of adequate thickness, preferably 1–2 mm, to be compressed when valve member 13 is assembled into circular recess 15 of housing 5. As shown in FIGS. 1–3, seal members 25 function to seal against irrigation and evacuation ports 7, 9 when they are obstructed by portions 17 of valve member 13. The exterior of valve member 13 is provided with a pair of lugs or ears to facilitate by way of mechanical advantage the manipulation of valve member 13 relative to housing 5.

FIG. 8 is a partial elevation view of housing 5 of irrigation and evacuation cannula 1 according to an additional embodiment of the present invention. In FIG. 8, housing 5 is illustrated without valve member (13 in FIGS. 1–7) rotatably received within circular recess 15. According to this embodiment of the present invention, a microswitch 31 is embedded in housing 5 beneath a flange (shown in FIGS. 1–3 and 6) carried by the valve member. Upon rotation of valve member 13, the flange engages microswitch 31 to actuate a suction or irrigation apparatus. Thus, the suction or irrigation apparatus is automatically actuated depending upon the position of valve member 13 relative to housing 5 and the configuration of irrigation and evacuation cannula 1.

Irrigation and evacuation cannula 1 is constructed of conventional materials for surgical instruments. Housing 5, sleeve member 3 and valve member 13 are formed of transparent or translucent polycarbonate to permit viewing of surgical instrument 51 and fluid flow through cannula 1 in operation. All elastomeric seals are formed of conventional materials and seals 25 are formed of the previously mentioned Santoprene™.

The irrigation and evacuation cannula according to the present invention provides a number of advantages. A principal advantage of the present invention is that it provides a cannula that is of simple design with relatively few moving parts. Another advantage is that fluid flows through the cannula in a relatively straight or linear fashion, avoiding the tortured flow paths provided in prior-art cannulae. This renders the cannula according to the present invention more efficient in operation, more easily cleaned, and less prone to clogging.

The invention has been described with reference to a preferred embodiment thereof. It is thus not limited, but is susceptible to variation and modification without departing from the scope of the invention.

We claim:

1. An irrigation and evacuation cannula for use in irrigating and evacuating a body cavity during surgery, said cannula comprising:
   a tubular sleeve member;
   a housing secured to said sleeve member and in fluid communication with said sleeve member;
   a first fluid port and a second fluid port, said first fluid port and said second fluid port formed in said housing opposite and in selective fluid communication with said sleeve member;
   a valve member carried by said housing for selectively obstructing one or more of said first and said second fluid ports;
   a circular recess in said housing for receiving said valve member;
   a venturi-shaped chamber within said housing, said chamber defined by cooperation of said valve member and said recess; and
   an instrument port including a seal member formed in said housing and aligned with said sleeve member, wherein a surgical instrument can be inserted through said instrument port, said housing said valve, and said sleeve member and into the body cavity, said valve member being operable with the surgical instrument disposed in the cannula.

2. The cannula according to claim 1 wherein the first and second fluid ports are irrigation and evacuation ports, respectively.

3. The cannula according to claim 2 further comprising:
   a switch member carried by the housing and cooperating with the valve member to selectively actuate a device external to the cannula responsive to movement of the valve member.

4. The cannula according to claim 1 wherein the seal member in the instrument port includes a lip seal and an outer-diameter seal.

5. The cannula according to claim 1 wherein the valve member is selectively removeable from the housing.

6. The cannula according to claim 1 in which a fluid flow path is selectively defined by the venturi-shaped chamber between the instrument port and the sleeve member, the fluid flow path being generally straight.

7. The cannula according to claim 1 further comprising:
   seal members disposed between the valve member and housing to seal the first and second fluid ports against loss.

8. The cannula of claim 1, wherein said first fluid port and said second fluid port are arranged about a circumference of said circular recess and on opposite sides of said instrument port.

9. An irrigation and evacuation cannula for use in irrigating and evacuating a body cavity during surgery, said cannula comprising:
   a tubular sleeve;
   a housing secured to one end of said sleeve, said housing including a circular recess in fluid communication with said sleeve;
   an instrument port with a seal member, said instrument port secured to said housing opposite and in alignment with said sleeve, said instrument port in fluid communication with said recess and said sleeve, wherein a surgical instrument can be inserted through said instrument port, said housing, and said sleeve;
   a valve member rotatably received in said circular recess of said housing, said valve member and said circular recess cooperating to define a venturi-shaped chamber; and
   suction and irrigation ports formed in said housing about the circumference of said recess, said venturi-shaped chamber selectively moveable into communication with one of said suction and irrigation ports.

10. The cannula according to claim 9 wherein the seal member in the instrument port includes a lip seal and an outer-diameter seal.

11. The cannula according to claim 9 wherein the valve member is selectively removable from the housing.

12. The cannula according to claim 9 in which a fluid flow path is selectively defined by the venturi-shaped chamber between the instrument port and the sleeve member, the fluid flow path being generally straight.

13. The cannula according to claim 9 further comprising:
   a microswitch disposed in said housing and partially projecting into said circular recess, said microswitch cooperating with said valve member to selectively actuate a device external to said cannula responsive to movement of said valve member in said circular recess.

14. The cannula according to claim 9 further comprising:
   seal members carried by the valve member to seal the suction and irrigation ports against loss.

15. An irrigation and evacuation cannula for use in irrigating and evacuating a bodily cavity during surgery, the cannula comprising:
   a housing including a valve recess, the housing including suction, fluid, and instrument ports in fluid communication with the valve recess;
   a sleeve member in fluid communication with the valve recess and coupled to the housing in general alignment with and generally opposite the instrument port;
   a valve member rotatably received in the valve recess of the housing, the valve member and valve recess cooperating to define a venturi-shaped chamber, the venturi-shaped chamber selectively movable into and out of fluid communication with the suction and fluid ports:
   a seal member disposed in the instrument port to seal against surgical instruments disposed in the instrument port and to seal the instrument port against fluid loss when no surgical instrument is disposed in the instrument port.

16. The cannula according to claim 15 wherein the seal member in the instrument port includes a lip seal and an outer-diameter seal.

17. The cannula according to claim 15 wherein the valve member is selectively removable from the housing.

18. The cannula according to claim 16 in which a fluid flow path is selectively defined by the venturi-shaped chamber between the instrument port and the sleeve member, the fluid flow path being generally straight.

* * * * *